US010879056B2

(12) United States Patent
Jo

(10) Patent No.: US 10,879,056 B2
(45) Date of Patent: *Dec. 29, 2020

(54) INTEGRATED DISEASE DIAGNOSTIC SYSTEM USING MATRIX-ASSISTED LASER DESORPTION/IONIZATION TIME-OF-FLIGHT MASS SPECTROMETER

(71) Applicant: ASTA, CO. LTD., Suwon (KR)

(72) Inventor: Eung Joon Jo, Old Tappan, NJ (US)

(73) Assignee: ASTA, Co. Ltd, Suwon (KR)

( * ) Notice: Subject to any disclaimer, the term of this patent is extended or adjusted under 35 U.S.C. 154(b) by 106 days.

This patent is subject to a terminal disclaimer.

(21) Appl. No.: 16/232,456

(22) Filed: Dec. 26, 2018

(65) Prior Publication Data

US 2019/0139747 A1 May 9, 2019

Related U.S. Application Data

(63) Continuation-in-part of application No. 14/679,114, filed on Apr. 6, 2015, now Pat. No. 10,197,551.

(60) Provisional application No. 62/005,392, filed on May 30, 2014.

(51) Int. Cl.
| | | |
|---|---|---|
| *H01J 49/00* | (2006.01) | |
| *H01J 49/16* | (2006.01) | |
| *G01N 33/49* | (2006.01) | |
| *H01J 49/40* | (2006.01) | |
| *G01N 33/483* | (2006.01) | |

(52) U.S. Cl.
CPC ...... *H01J 49/0036* (2013.01); *G01N 33/4833* (2013.01); *G01N 33/49* (2013.01); *H01J 49/0009* (2013.01); *H01J 49/164* (2013.01); *H01J 49/40* (2013.01)

(58) Field of Classification Search
CPC ..... G01N 33/4833; G01N 33/49; H01J 49/40; H01J 49/164
USPC ........................................ 250/281, 282, 288
See application file for complete search history.

(56) References Cited

U.S. PATENT DOCUMENTS

| | | | |
|---|---|---|---|
| 6,983,213 B2 | 1/2006 | Wang | |
| RE39,353 E | 10/2006 | Vestal | |
| 10,197,551 B2 * | 2/2019 | Jo | ...................... G01N 33/4833 |
| 2009/0127454 A1 | 5/2009 | Ritchie et al. | |
| 2015/0136972 A1 | 5/2015 | Lasch et al. | |

* cited by examiner

*Primary Examiner* — Michael Maskell
(74) *Attorney, Agent, or Firm* — AJU Kim, Chang & Lee

(57) ABSTRACT

A disease diagnostic system where a sample preparation unit and/or a matrix-assisted laser desorption/ionization time-of-flight mass spectrometer (MALDI-TOF MS) data generation unit may be integrated in one system or a set of a system to improve the user-friendliness of the system. The system may include a sample preparation unit with processing modules and/or a handler to move samples in an autonomous manner to enhance reproducibility of measurement data and/or user-friendliness. A different set of processing modules may be selected for a particular disease type (e.g. such as cancer) to be diagnosed. The system may be used to identify biomaterials such as bacteria, virus, and fungi from body fluids like blood, urine, and saliva and other cells.

20 Claims, 13 Drawing Sheets

Figure 1:
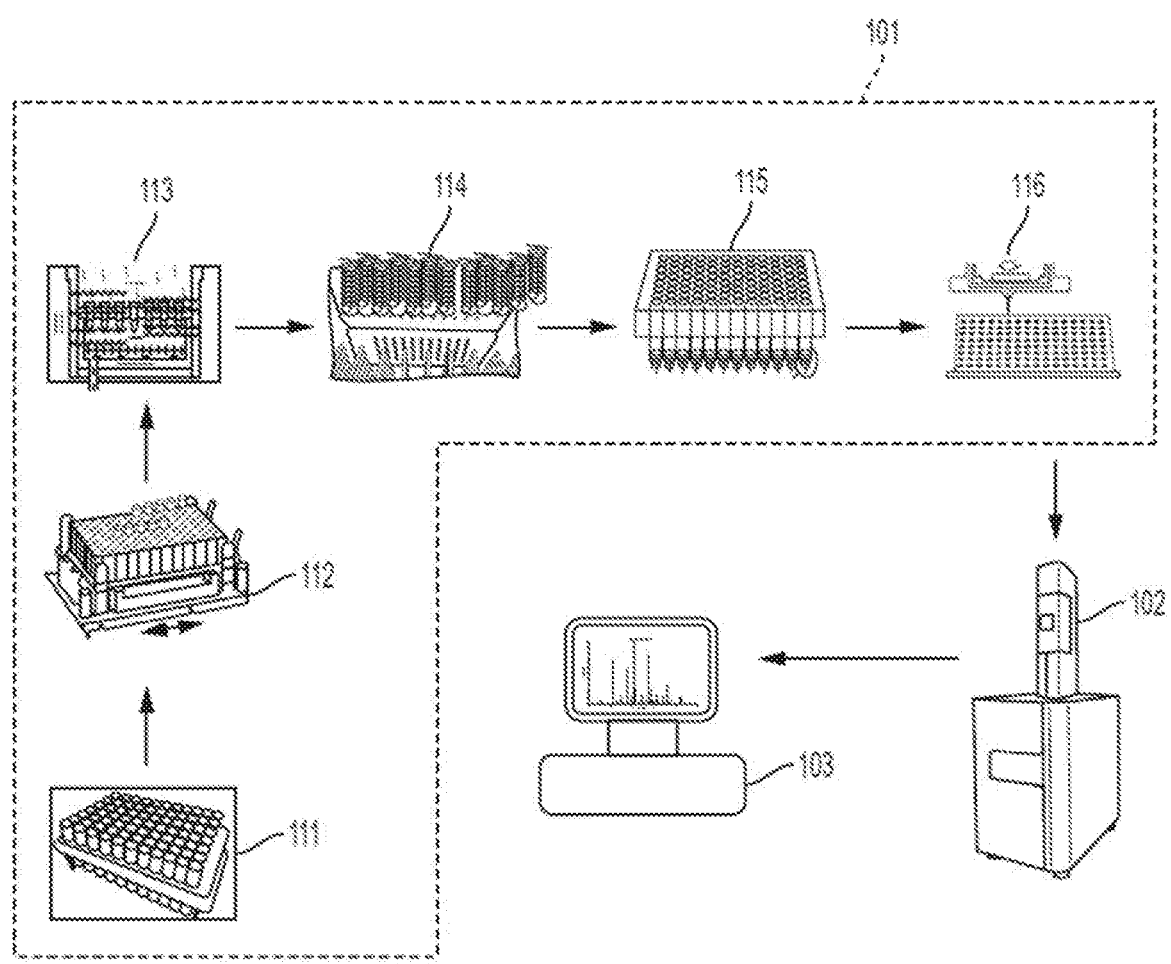

INTEGRATED DISEASE DIAGNOSTIC SYSTEM USING MATRIX-ASSISTED LASER DESORPTION/IONIZATION TIME-OF-FLIGHT MASS SPECTROMETER

The present application claims priority to U.S. Provisional Patent Application No. 62/005,392 filed on May 30, 2014 and U.S. patent application Ser. No. 14/679,114 filed on Apr. 4, 2015, which are hereby incorporated by reference in their entireties.

BACKGROUND

A biomarker is a biological molecule found in blood, other body fluids, or tissues that is a sign of a normal or abnormal process, or of a condition or disease. For example, a glycoprotein CA-125 is a biomarker that signals the existence of a cancer. Hence, biomarkers are often measured and evaluated to identify the presence or progress of a particular disease or to see how well the body responds to a treatment for a disease or condition. Existence or a change in quantity level of biomarkers in proteins, peptides, lipids, glycan or metabolites can be measured by mass spectrometers.

Among numerous types of mass spectrometers, Matrix-Assisted Laser Desorption/Ionization Time-of-Flight Mass Spectrometry (MALDI-TOF MS) is an analytical tool employing a soft ionization technique. Samples are embedded in a matrix and a laser pulse is fired at the mixture. The matrix absorbs the laser energy and the molecules of the mixture are ionized. The ionized molecules are then accelerated through a part of a vacuum tube by an electrical field and then fly in the rest of the chamber without fields. Time-of-flight is measured to produce the mass-to-charge ratio (m/z). MALDI-TOF MS offers rapid identification of biomolecules such as peptides, proteins and large organic molecules with very high accuracy and subpicomole sensitivity. MALDI-TOF MS may be used in a laboratory environment to rapidly and accurately analyze biomolecules and expanding its application to clinical areas such as microorganism detection and disease diagnosis such as cancers.

Disease diagnosis using MALDI-TOF MS in a clinical environment, however, presents several problems. One problem is poor reproducibility of the mass analysis data. In particular, sample preparation process is a major factor affecting data reproducibility of MALDI-TOF MS, where a specific target material is extracted from an original sample, mixed with a matrix and then loaded onto a sample plate. Handling processes may inevitable involve human intervention where a person manually moves samples from one processing step to another processing step and/or performs a number of experimental processes. This makes the data susceptible to uncontrolled external influences, which leads to poor homogeneity or separability of a sample and a risk of sample contamination.

Another factor affecting data reproducibility is the measurement sensitivity or measuring process of the MALDI-TOF MS system itself. While MALDI-TOF MS can analyze samples fast with high sensitivity so that it would be an excellent tool for clinical application, it may be a relatively poor quantitative analyzer because Relative Standard Deviation (RSD) of detected signal intensities is relatively high due to its nature of ionization process using organic matrix. Even though the MALDI-TOF MS system adopts a delayed extraction technique, it may be challenging to have all the particles of a mass get the same kinetic energy just before entering a field-free zone in the chamber. It may be an inevitable data spread source.

In addition to the low reproducibility issue, disease diagnosis using MALDI-TOF in a clinical environment may present cost issues, maintenance issues, and/or difficulties in sample preparation. Some systems may be too expensive and bulky to be used in a clinical environment and/or too difficult to use for point-of-care testing ("POCT") and/or onsite care. To be used in a clinical and/or POCT/Onsite care environment, an entire system may need to be compact, easy to manage, capable of generating more reproducible data, and/or having a relatively low cost.

SUMMARY

Embodiments relate to disease diagnosis. Some embodiments specifically relate to mass data based disease diagnosis using matrix-assisted laser desorption/ionization time-of-flight Mass Spectrometry (MALDI-TOF MS).

Embodiments relate to an integrated disease diagnosis system where a sample preparation unit and a MALDI-TOF MS unit are integrated in one system. A MALDI-TOF MS unit may be structurally modified for clinical purposes to reduce its volume and/or weight and/or to simplify the components into the modules so that maintenance work is reduced. A diagnosis system may include a diagnosis software unit, which compares the spectra of test data with pre-stored spectra to analyze the pattern difference and identify presence and progress of a disease, for onsite-care or point-of-care. The sample preparation unit may include a set of processing modules and a handler to move samples between modules in an autonomous manner. A different set of processing modules may be selected for diagnosing a particular disease type. The sample preparation process may be automated to improve reproducibility and usability of MALDI-TOF MS analysis. Embodiments may improve the identification accuracy of the existence and quantity variations of proteins, DNAs, RNAs, and/or other biomaterials in body fluids or cells by MALDI-TOF MS and/or other mass spectrometers. Embodiments may be used to identify disease types like cancers as well as types of bacteria, archaea, protozoa, viruses, and/or fungi.

In embodiments, a MALDI-TOF MS unit may include a data storing device on which signals acquired from each laser irradiation onto a spot of a sample plate of MALDI-TOF MS are stored for data reproducibility. The stored irradiation signals may be calibrated by filtering out non-reproducible measurement data for better reliable and/or reproducible result.

In embodiments, to use MALDI-TOF MS for a disease diagnostic system, the MALDI-TOF MS system may generate more reproducible data by optimized reproducibility in a data-monitoring system in which the data acquired from each module is recorded and monitored in advance before they give wrong input for diagnosis. In embodiments, the MALDI-TOF MS system may be modularized into components sets to reduce maintenance work for the machine reliability, price control, volume minimization, and/or weight minimization of the system.

Integration of the automatic sample preparation unit into MALDI-TOF MS may enhance user-friendliness and/or optimized data reproducibility, in accordance with embodiments. Components of MALDI-TOF MS may be divided into several modules, where signals from each module and/or signals of components in each module are recorded and compared with standard normal signals for remote and/or online maintenance.

DRAWINGS

Example FIG. 1 is an arrangement of a disease diagnosis laboratory where a sample processing unit, a MALDI-TOF MS unit, and a diagnosis unit are separated in three different systems, in accordance with embodiments.

Figure 2:
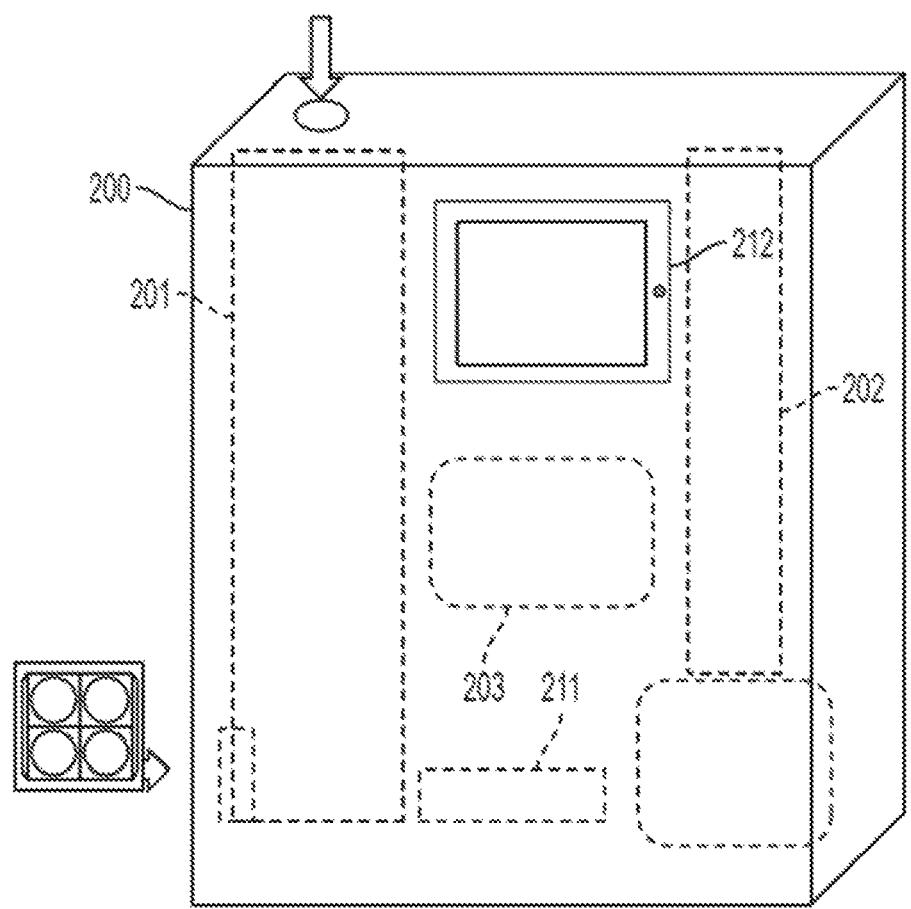

Example FIG. 2 is a system diagram including a sample processing unit, a MALDI-TOF MS unit, and a diagnosis unit integrated into one system, in accordance with embodiments.

Figure 3:
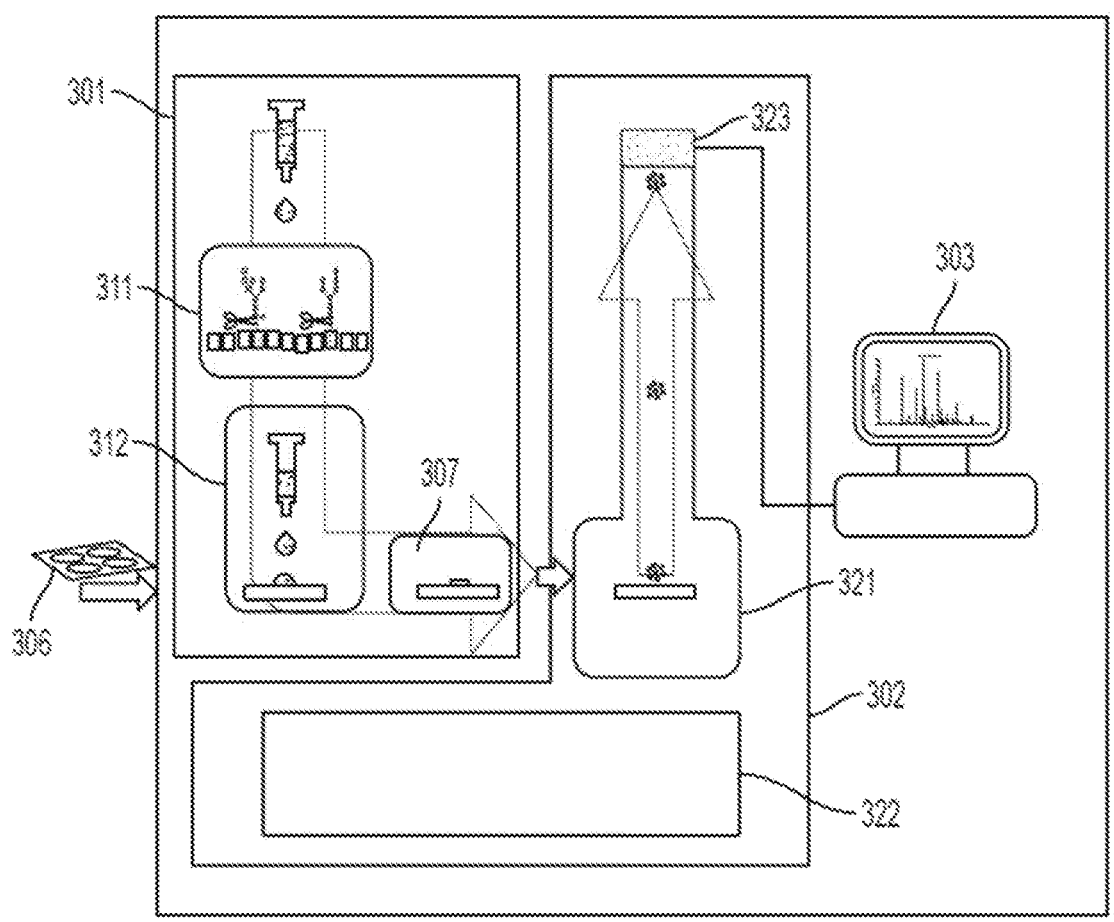

Example FIG. 3 is a system diagram of the integrated system including a sample processing unit, a MALDI-TOF MS unit, and a diagnosis unit in one system, in accordance with embodiments.

Figure 4:
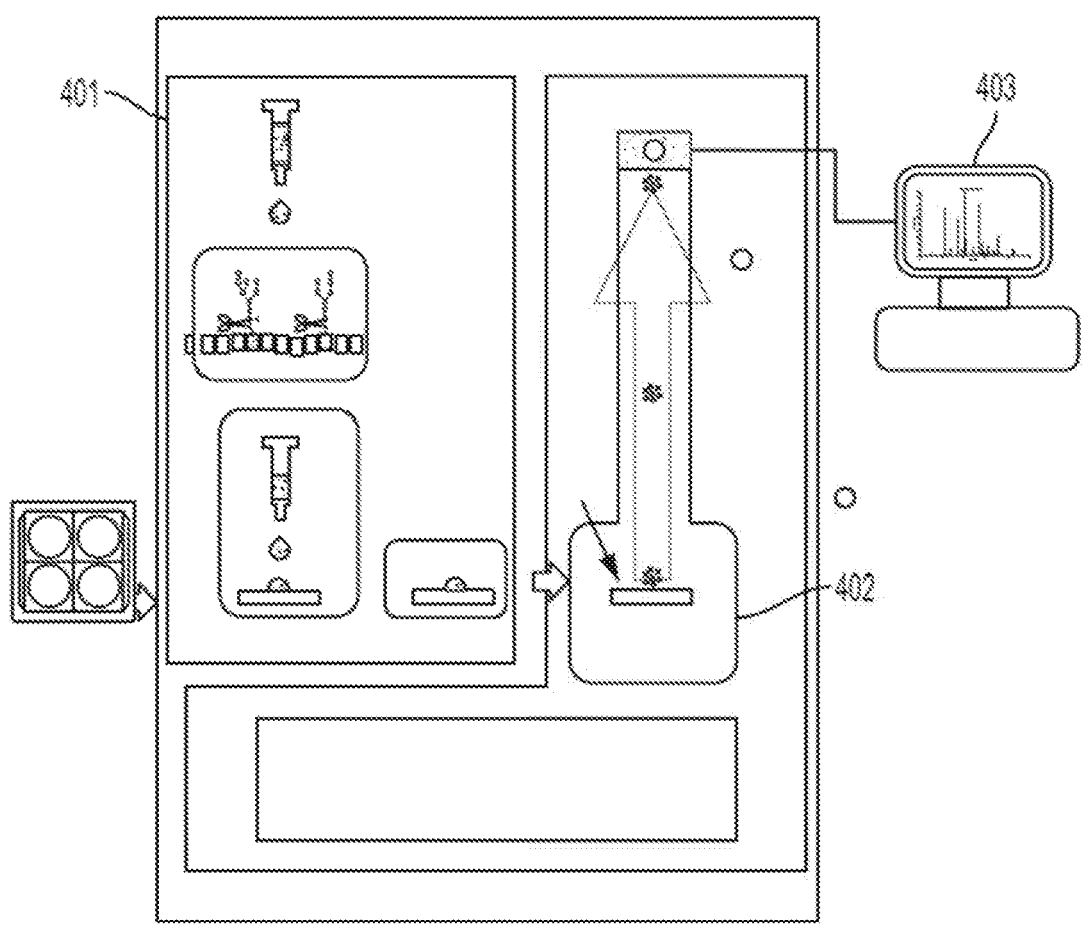

Example FIG. 4 is a system diagram of an integrated diagnostic system including a sample processing unit and a MALDI-TOF MS unit integrated in one system, whereas a diagnosis unit is provided as a separate unit, in accordance with embodiments.

Figure 5:
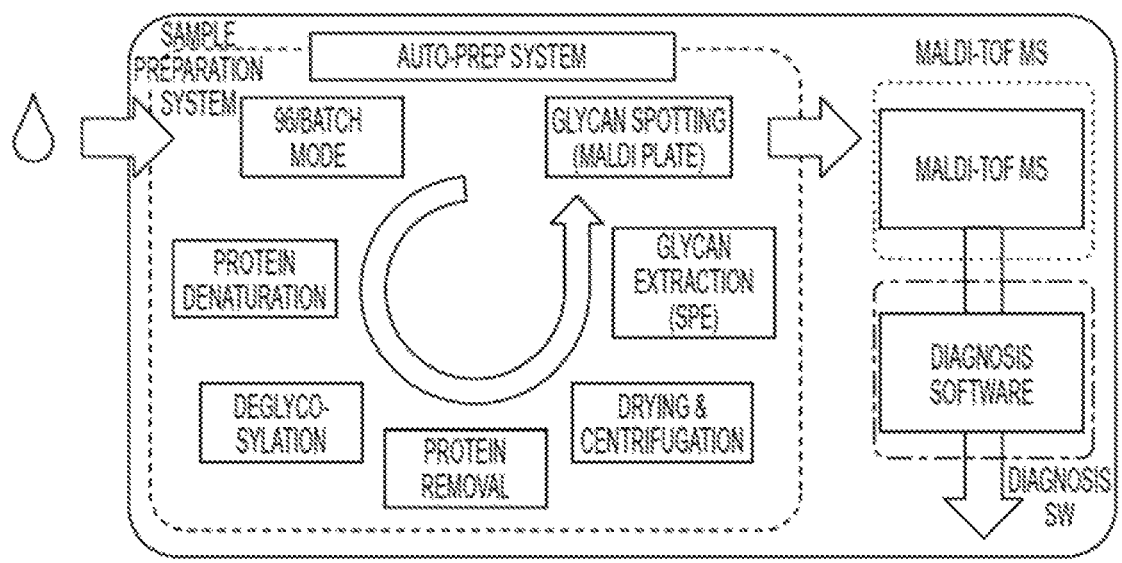

Example FIG. 5 is an example of a sample processing flow, in accordance with embodiments.

Figure 6:
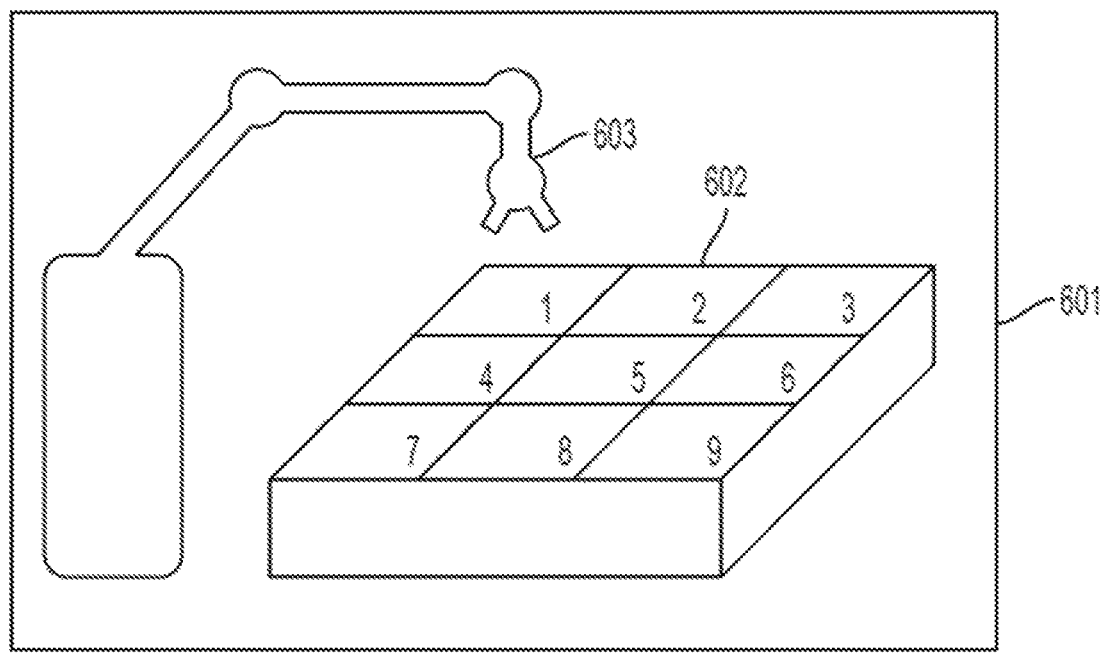

Example FIG. 6 is a system diagram of an automatic sample processing unit having a set of processing modules arranged in a horizontal structure and a robotic arm to move samples between the modules, in accordance with embodiments.

Figure 7:
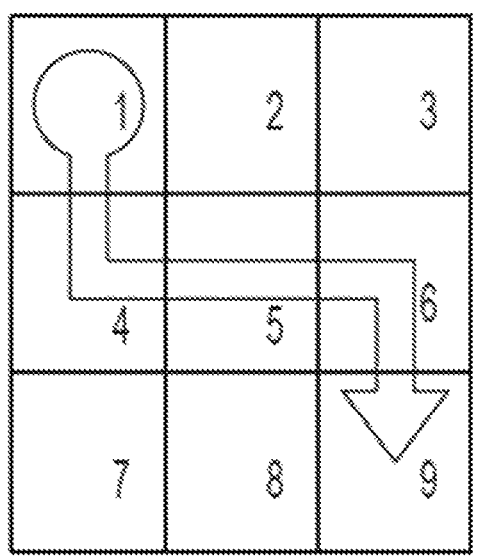

Example FIG. 7 illustrates sample processing modules selected for a particular disease type, in accordance with embodiments.

Figure 8:
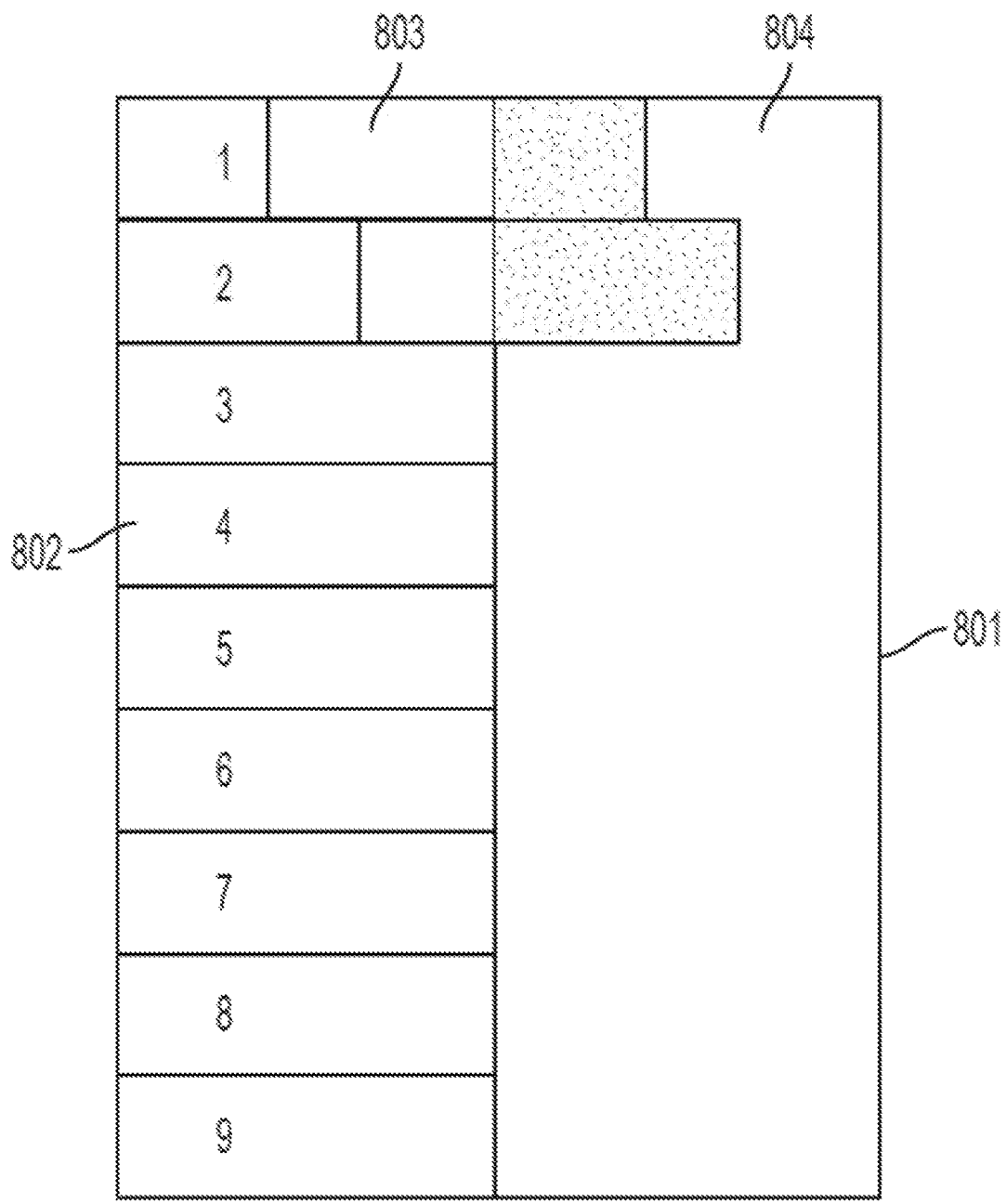

Example FIG. 8 is an automatic sample processing unit having a set of processing modules arranged in a vertical structure and with a sliding arm, in accordance with embodiments.

Figure 9:
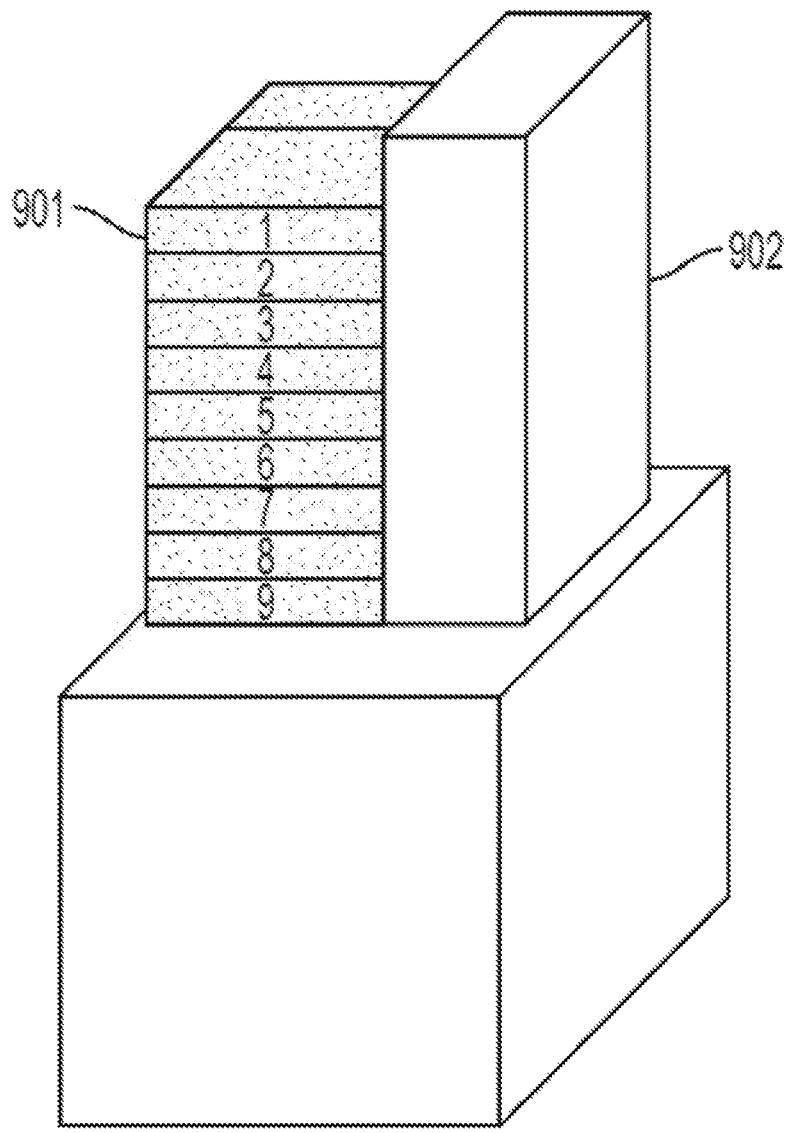

Example FIG. 9 illustrates a vertical-structure automatic sample processing unit and a MALDI-TOF MS unit that are integrated, in accordance with embodiments.

Figure 10:
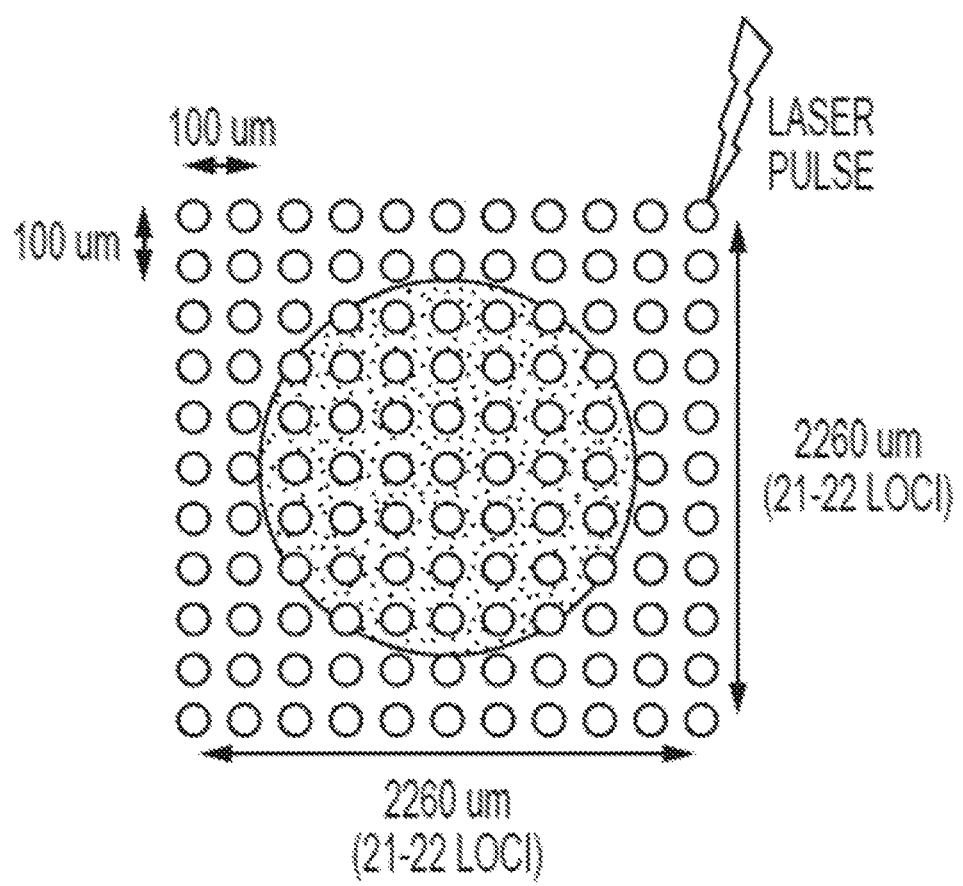

Example FIG. 10 illustrates a MALDI Plate where a spot on a sample plate is irradiated by a laser pulse, in accordance with embodiments.

Figure 11:
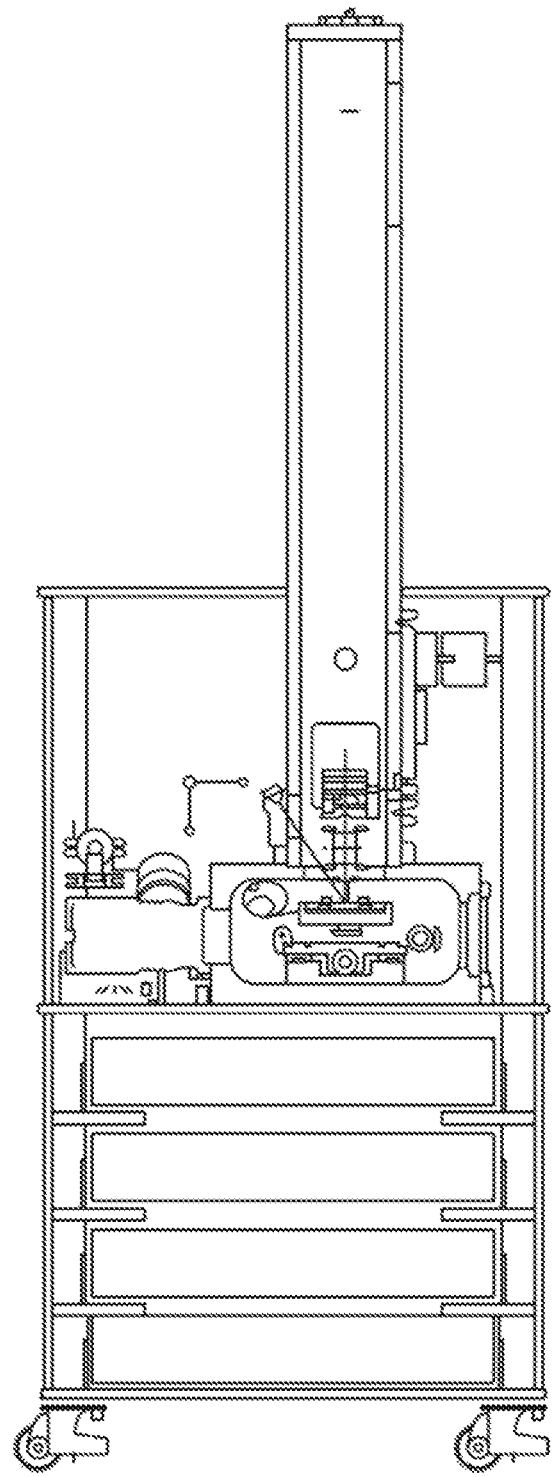

Example FIG. 11 is a schematic view of a MALDI-TOF MS unit in which components are in modules, in accordance with embodiments.

Figure 12:
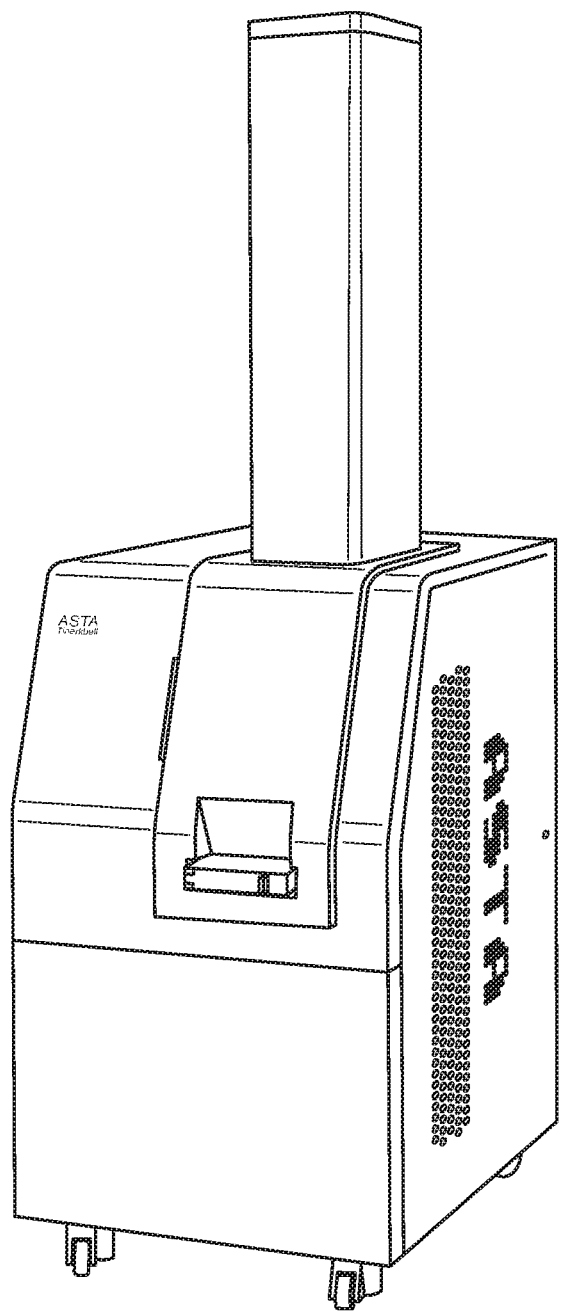

Example FIG. 12 illustrates a floor-supported MALDI-TOF MS unit, in accordance with embodiments.

Figure 13:
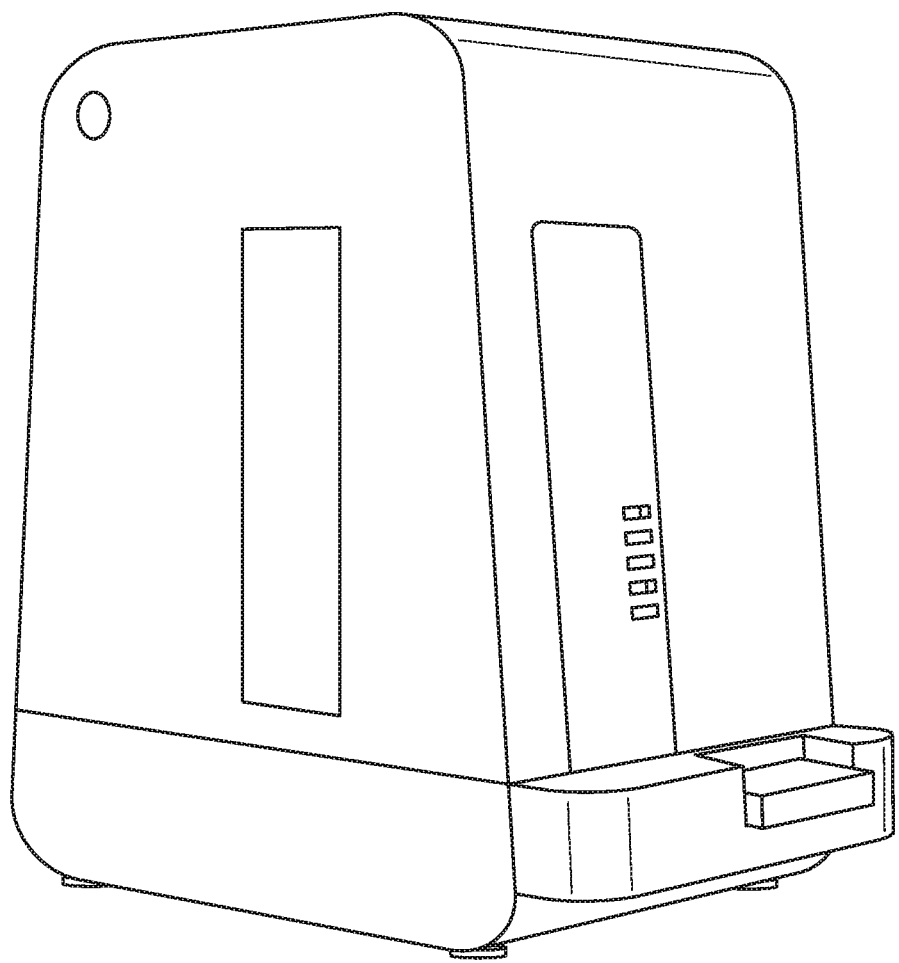

Example FIG. 13 illustrates a benchtop MALDI-TOF MS unit, in accordance with embodiments.

DESCRIPTION

Example FIG. 1 illustrates a disease diagnosis laboratory where a sample processing facility (101) includes multiple sample processing tools, a MALDI-TOF MS system (102), and a diagnosis software system (103), which are separated from each other, in accordance with embodiments. To extract a glycan for an ovarian cancer diagnosis, for example, a patient's serum is entered into a multi-well plate (111) to undergo a sample reception process and a protein denaturation process (112), followed by a deglocosylation process using enzyme (113). A protein removal process (114), a drying and centrifugation process, a glycan extraction process (115), and a spotting process (116) then follow. The spotted samples are analyzed by the MALDI-TOF MS system (102) to generate at least one glycan profile. The diagnosis software (103) compares the glycan profile of the sample with the pre-stored glycan profile or profiles to identify the presence and progress of ovarian cancer.

Example FIG. 2 shows an integrated disease diagnosis system using MALDI-TOF, in accordance with embodiments. The system (200) includes of an automatic sample preparation unit (201), a MALDI-TOF MS unit (202), and a disease diagnosis unit (203), all integrated into one integrated system. The sample preparation unit (201) prepares a patient's sample, which are transferred to the MALD-TOF MS unit (202) through automatic transporting means such as a conveyor (211). The MALDI-TOF MS unit (202) analyzes the sample and generates the mass information of the sample. The disease diagnosis unit (203) then identifies the presence and progress of the disease, and show the result in the monitor screen (212).

Embodiments identifies the existence and quantity variations of proteins, RNAs, DNAs in blood, urine, and other biomaterials such as microorganisms, in an autonomous manner by touching input monitor screen only (212). Embodiments may be used to identify diseases including cancers and microorganisms such as bacteria, archaea, protozoa, viruses, and fungi.

Example FIG. 3 shows the integrated disease diagnosis system, in accordance with embodiments. Samples may undergo a combination of process by selected modules. In the sample preparation system (301), a sample goes through a predefined and preprogrammed sequence depending on diagnosis or screening purposes in an automatic sample preparation unit (311). In embodiments, for glycan extraction, multiple processing modules may be selected, which as sample reception, protein denaturation, deglycosylation, protein removal, drying, centrifugation, solid phase extraction, and/or spotting. After sample preparation, the sample loader (312) loads the samples onto the plates (306) and are dried in a sample dryer (307).

The samples may then be provided to the MALDI-TOF MS unit (302) having a ion flight chamber (321) and/or a high voltage vacuum generator (322), in accordance with embodiments. A processing unit (323) in the MALDI-TOF MS may identify the mass/charge and its corresponding intensity. For the disease diagnostic purpose, those acquired mass and intensity data may be reorganized to set up a standard mass list, in which a concept of the center of mass where intensities are balanced and equilibrated is introduced. A standard mass to charge list is defined based upon the machine accuracy and the center of mass concept. The stored spectrum data for each laser irradiation may also be used to set up the standard mass list. The diagnostic unit (303) may then compare, the spectra from a patient's sample with the pre-stored spectra and analyzes the pattern difference of the two spectra. The diagnostic unit may then identify the presence and progress of the disease.

Example FIG. 4 illustrates an integrated disease diagnosis system where the sample preparation unit (401) and the MALDI-TOF (402) are integrated, with the diagnosis unit (403) stands apart as a separate unit, in accordance with embodiments.

Example FIG. 5 illustrates an automatic preparation system, in accordance with embodiments. Each processing module may be one of a drying module, a microwave enzyme digestion module, a hot water bath module for denaturation, and/or a spotting module. A robotic arm may be used for transferring sample vials from one module to another to perform a sequence of pre-programmed functions of sample protocol. The sample may undergo a pre-programmed sequence of modules depending on a particular diagnostic purpose. Once a user enters an instruction on the touch screen, the rest of the functions are performed automatically by a system module controller with pre-programmed algorithms, in accordance with embodiments.

In embodiments, the sample preparation procedure may be a significant factor affecting data reproducibility of MALDI-TOF MS. A specific target material may be extracted from an original sample, mixed with a matrix and then loaded onto a sample plate. Experimental errors may be caused when a person manually performs the function of each module and moves samples from one processing step to another processing step. The automatic sample processing unit, in accordance with embodiments, may significantly reduce such errors coming from manual sample preparation and thus enhance the reproducibility of the MALDI data.

Once a user selects a particular disease type, the system itself may select the modules to be employed, in accordance with embodiments. An automatic transport means such as a robotic arm or a sliding arm may be used for transferring samples into different modules to perform pre-programmed functions. As a result, in accordance with embodiments, the system may be easy to use and easy to maintain.

Example FIG. 6 illustrates an automatic sample preparation unit (601) with processing modules (602) in a horizontal structure and a robotic arm (603) for picking and transferring the sample from one processing module to another, in accordance with embodiments. A sample preparation process may be divided into modular processes. Depending on a disease type, a different combination of modular processes may be selected to be employed. For example, in accordance with embodiments, for glycan extraction, the following modular processes are selected: a sample reception process, a protein denaturation process, a deglycosylation process, a protein removal process, a drying & centrifugation process, a solid phase extraction process, and/or a spotting process. In embodiments, one or more modular processes may be skipped, or an extra process (e.g. a culturing process) may be added.

Example FIG. 7 shows an example of a preparation processing sequence performed by the robotic arm, in accordance with embodiments. For example, modules 1-4-5-6-9 may be selected.

Example FIG. 8 illustrates the automatic sample preparation unit (801) where the processing modules (802) are arranged in a vertical structure, in accordance with embodiments. The structure is composed of two columns in which one column (803) makes up sample preparation modules and the other column (804) is used as a workspace for operating the robotic arm and for performing the function of a module.

Example FIG. 9 illustrates integrating a vertical-structure automatic sample processing unit (901) and the MALDI-TOF MS (902) unit to make the whole system compact, in accordance with embodiments.

Higher accuracy in MALDI-TOF MS data may be achieved by implementing an algorithm which finds standard masses and highly reproducible intensity data. Reproducibility may be measured by the Relative Standard Deviation (RSD) of a measurement data set. RSD is the standard deviation of intensity divided by the average intensity of a MALDI-TOF mass spectrum peak. Embodiments may reduce the RSD by minimizing errors in sample preparation step through automatic processing flow and optimizing acquired measurement data through filtering data obtained from laser irradiations on a spot.

For example, protocols involving the ovarian cancer classification, may have an improved RSD (from 25% to 10%) by automating sample preparation, in accordance with embodiments.

Automation of sample preparation for MALDI-TOF MS analysis may be significant in diagnosis of early-stage disease, such as cancer. In embodiments, benign ovarian tumors and borderline ovarian tumors of ovarian cancer may be successfully classified when the technique of semi-automated sample preparation is applied. Enhancement of reproducibility may be achieved by using a matrix-prespotted MALDI plate and an automation process, in accordance with embodiments, compared to other methods in which a matrix was mixed with serum glycan analytes and manually loaded onto MALDI target plate. In embodiments, automated sample preparation may be able to lower the RSD of MALDI-TOF MS data by at least approximately 10%. Consequently, screening accuracy of benign tumors and borderline tumors may be above approximately 75%, which implies that the classification accuracy between an early stage cancer patient and a person without ovarian cancer may be greater than 75%, in accordance with embodiments.

Embodiments relate to a MALDI-TOF MS data generation unit to increase data reproducibility. Some MALDI-TOF MS devices use a sum or an average value of the data spotting on a specific sample spot of a plate. Embodiments include a calibration unit to correct the spotting data using a statistical method to increase the reproducibility of the data. For example, the data on a spot may not be uniform. The uniformity might be higher in a liquid form of the sample. However, a sample is prepared in a solid form on a sample plate, then converted to a gaseous state to be analyzed intrinsically may cause relatively lower uniformity, which in turn may degrade reproducibility of the mass data. Therefore, the data acquired during laser spotting on the same spot should be carefully examined and calibrated for high reproducibility.

Embodiments store data for each laser irradiation in a MALDI-TOF MS and calibrate intensities by eliminating the outliers of the intensity data for each mass-to-charge (m/z) peak or selecting a data set which shows the lowest RSD. Elimination may be done with an algorithm by which some percentages of the data shall be eliminated before averaging or summation of the intensities, in accordance with embodiments. The percentage of elimination may be determined by at least one predefined rule to minimize the RSD of the intensities.

FIG. 10 shows that a laser pulse is irradiating a spot on a sample plate, in accordance with embodiments. Each time a laser pulse is fired on a spot, a spectrum of peaks may be created. Due to non-homogenous nature of drying sample and matrix mixture on a sample plate, intensities may vary depending on a spot hit by a laser beam. Measured mass values and corresponding intensities may fluctuate with shots.

In accordance with embodiments, a disease diagnostics software or microorganism identification software include aspects of the following algorithm: The mass values by a single pulse of laser are stored on a data storage space in MALDI-TOF MS system without adding to or averaging with the data obtained from other laser irradiations. AND/OR The stored mass and intensity data may then be analyzed and/or filtered out depending upon the characteristics of the analysis of diseases. AND/OR The stored mass value may be inherently broad for each mass so that the authentic mass value for each mass in a spot of a sample plate is estimated as described below for the analysis of disease identification or microbial tests. AND/OR Since every laser shot yields a slightly different authentic mass value, each authentic mass may be adjusted to the corresponding standard mass value for diagnostic purposes. AND/OR The measured intensity values are then normalized and calibrated for each standard authentic mass. The stored intensity data for each laser shot may then be put together into its distribution curve for filtering out to reduce the RSD of the data.

Embodiments relate to finding authentic mass and/or center of mass in a single laser shot. All the particles of the same mass may drift into the field-free chamber of MALDI-TOF MS with the same velocity, but in some circumstances may deviate from the velocity of the authentic mass. The mass data obtained from a detector may be calibrated for diagnostic and/or other applications to obtain standard mass by authentic mass and/or center of mass information based on certain observations, in accordance with embodiments.

In embodiments, observations may relate to a deviation from the authentic mass due to inherent nature of ions that can be denoted as $I_i*(m_i-m_c)$, where $m_i$ is a measured mass with an intensity $I_i$, and $m_c$ is the authentic mass or the center of mass. Since the intensity $I_i$ is related to the number of particles of the mass, $m_i$, the quantity $I_i*m_i$ may be closer to the quantity of the specific mass $m_c$, rather than $m_i$ itself or $I_i$ itself. The sum of the quantity $\Sigma I_i*m_i$ can be defined as $m_c I_c$ where $I_c$ is $\Sigma I_i$, and $m_c=\Sigma I_i*m_i/\Sigma I_i$. This may be equivalent to $\Sigma I_i*(m_i-m_c)=0$, meaning that the ion particles are distributed and equilibrated around the center of mass. Therefore, in embodiments, the authentic mass or the center of mass, $m_c$, can be estimated using the intensity weighted mass formula, $m_c=\Sigma Ii*m_i/\Sigma_i$ as the definition above. In other words, $m_c$ may be a weighted sum of all the masses around a specific (m/z) of interest. The number of intensities for a mass/charge is selected based on the accuracy of a MALDI-TOF MS, in accordance with embodiments.

Embodiments relate to calibration of (m/z)'s and intensities within a single MALDI plate spot. Matrix solution mixed with a sample may be spotted on a MALDI plate, typically made of metal. A MALDI plate may include multiple spots containing matrix solution mixed with a sample. Laser pulses may be fired multiple times at each spot. Because the solution densities may not be uniform even within a spot and the part of the sample and matrix mixture after a laser irradiation may have a different structure from the one just before the previous laser irradiation, intensity variations for each laser irradiation may be natural and/or inevitable. Such intensity deviations within a spot of a MALDI-plate may be calibrated by a filtering algorithm for each m/z's intensity distribution from the storing data of each laser irradiation.

Each time a laser pulse is fired on a spot of a MALDI plate, a spectrum of peaks may be created, in accordance with embodiments. For each peak of the spectrum, there may be a list of peaks acquired from each laser pulse irradiation. For example, if the irradiation is 1,000 times, the number of peaks for a mass-to-charge (m/z) shall be 1,000 if all the peaks are above noise threshold level. Those (m/z)'s of relatively slight differences may be calibrated to the corresponding standard mass/charge (m/z).

In embodiments, the intensity weighted masses for each mass may be calibrated to a standard mass for diagnostic purposes such as micro-organisms detection and/or cancer marker identification. A standard mass may be a mass representing a mass bracket, where a mass bracket is a range of masses in which all the masses are the identical mass called standard mass for the bracket.

A standardized mass-to-charge ratio (m/z) library may be created, in accordance with embodiments. The range of a first mass bracket may be the measuring time interval (e.g. time bin of the detection system of MALDI-TOF MS). Since the ions with the same mass may have different initial velocity at the entrance the field-free chamber of MALDI-TOF MS, some of the mass brackets may need to be merged as an identical entity (e.g. those brackets may be assumed to be an identical mass bracket). The merge guideline for a second mass bracket may be based on average mass accuracy (e.g. 100 ppm of a mass). In this example, any mass within 100 ppm of a specific mass may be regarded as the same mass of that specific mass.

Another merge guideline example for a second mass bracket is to use a modified uniform interval for the first range and then employ a concept of difference comparison in which a mass of a bracket and another mass of the adjacent bracket are compared and merged if the difference of two masses is within the modified uniform bracket interval. For example, a table may be generated containing brackets with base (m/z) ranging from 0 to 50,000 (or any relatively high number), each bracket having a range of (m/z)'s with an interval of 0.001 (modified uniform interval), where machine accuracy error (in this example) is assumed to be greater than 1 ppm for 1,000 so that 0.001 covers most of all machine errors in presence. If the minimum intensity of a bracket minus the maximum intensity of the bracket prior to the bracket of interest is less than the pre-set machine accuracy error (e.g. 0.001 or second decimal points, 0.01), then those brackets are merged into one, labeled with a median value of the merged ranges.

If there are two or more known (m/z)'s in any bracket range, such bracket may be split into two or more sub-brackets. For example, if an example median contains two or more known (m/z)'s in nature, then the bracket represented by that median split into two or more sub-brackets.

Embodiments relate to calibration of intensities within a single MALDI plate spot. Any m/z may be adjusted to the standardized m/z, in accordance with embodiments. After all the acquired intensities are rearranged for the standard m/z, each standard m/z may have its own m/z range and corresponding intensity obtained from each laser pulse irradiation. Each standard m/z may have an intensity distribution containing outliers of an abnormal character. For example, a parameter table of 1,000 laser irradiation can be constructed. In embodiments, a rounded intensity value may be rounded down to two decimal places, if the machine error is 10 ppm for 1,000 of m/z.

Several filtering guidelines may be employed to minimize the RSD, in accordance with embodiments. For example, 90% of the high intensities may be selected to be the intensities of (m/z) if its average RSD is the minimum. Abundance (frequency of a range) or intensity level may be one of the candidates for a filtering guideline, in accordance with embodiments.

Embodiments relate to calibration of intensities to reduce spot-to-spot variation. The intensities of a mass spectrum may vary from one spot to another within a plate. Spot-to-spot variation may be reduced by scaling or normalizing the intensities according to a scale factor or a normalization factor that results in the minimum average RSD. Average RSD may also be different depending on a method of selecting peaks. Thus, according to embodiments, an average RSD for each scale/normalization factor and each method of selecting peaks may be obtained, and then the scale/normalization factor and the method that can minimize the average RSD is selected.

In embodiments, with an automated procedure of sample preparation and/or calibration methods, there may be significant enhance the reproducibility of the MALDI-TOF MS for a diagnostic purpose, such a cancer diagnosis.

Example FIGS. 11 and 12 illustrate a floor-supported MALDI-TOF MS unit, in accordance with embodiments. Example FIG. 13 illustrates a benchtop MALDI-TOF MS unit, in accordance with embodiments. Although variations of specific form factors are anticipated in accordance with embodiments, both a floor-supported and benchtop design may be implemented in accordance with embodiments. In some embodiments, floor-supported MALDI-TOF MS units may have advantages such as customer convenience, manufacturing techniques, component costs, performance advantages, and other attributes. In some embodiments, benchtop MALDI-TOF MS units may have advantages such as customer convenience, manufacturing techniques, component costs, performance advantages, and other attributes. For example. Benchtop MALDI-TOF MS units may be integrated into laboratory space in doctors' offices with other benchtop, desktop, or countertop types of equipment. Other general form factors of MALDI-TOF MS units aside from floor-supported and benchtop MALDI-TOF MS units may be appreciated within the spirit of embodiments.

It will be obvious and apparent to those skilled in the art that various modifications and variations can be made in the embodiments disclosed. This, it is intended that the disclosed embodiments cover the obvious and apparent modifications and variations, provided that they are within the scope of the appended claims and their equivalents.

What is claimed is:

1. A system comprising:
a control system comprising a processing unit and a storage unit, wherein the storage unit comprises a protocol executed by the processing unit;
a Matrix-Assisted Laser Desorption/Ionization Time-of-Flight Mass Spectrometry (MALDI-TOF MS) unit, wherein the MALDI-TOF MS unit is configured to conduct at least one measurement on a sample,
wherein the control system is configured to calculate a representative mass of the sample among neighboring masses using center of mass information, and
wherein the center of mass information comprises an intensity weighted sum of masses around a specific mass-to-charge ratio of interest.

2. The system of claim 1, wherein the control system performs at least one of:
disease diagnostics;
microorganism identification;
calibrating mass/charge; or
calibrating intensity data by standard mass analysis through weighted intensity and bracket comparison with normalization through minimum relative standard deviation thresholds by identifying differences in signals of mass and intensity to diagnose at least one disease and identification of at least one microorganism or biomaterial.

3. The system of claim 2, wherein at least one of:
the biomaterial comprises microorganisms including bacteria;
the biomaterial comprises a virus;
the biomaterial comprises body fluid including blood or cells;
the biomaterial comprises cancer cells;
the at least one disease is a cancer; or
the sample contains a glycan.

4. The system of claim 1, wherein the control system comprises:
a unit for generating a standard mass-to-charge library to correct the at least one measurement on the sample.

5. The system of claim 1, wherein the control system comprises at least one of:
a filter for filtering out erroneous data outside a credibility range;
an analysis unit for producing a representative reproducible value from the filtered data; or
an averaging unit for producing a representative value from the filtered data.

6. The system of claim 1, wherein the system comprises:
a calibration unit with laser-shot independent data storing space for calibrating the at least one measurement received from the MALDI-TOF MS unit to minimize measurement deviation; and
an interface unit configured to receive calibrated data and using the calibrated data to identify at least one disease by comparing the at least one measurement with known disease patterns.

7. A method comprising:
processing a sample containing a biomaterial;
generating mass measurement data using at least one Matrix-Assisted Laser Desorption/Ionization Time-of-Flight Mass Spectrometry measurement of the sample; and
calibrating the mass measurement data, wherein the calibrating comprises calculating a representative mass of the sample among neighboring masses using center of mass information, and
wherein the center of mass information comprises an intensity weighted sum of masses around a specific mass-to-charge ratio of interest.

8. The method of claim 7, wherein:
the calibrating the mass measurement data comprises calculating the center of mass information from mass measurements dispersed due to interference among neighboring ions of the sample; and
the calibrating the mass measurement data uses the center of mass information as representative mass information.

9. The method of claim 7, wherein the calibrating the mass measurement data comprises:
creating a standard mass-to-charge ratio library;
calibrating the mass measurement data using the standard mass-to-charge ratio library; and
calibrating intensities of the mass measurement data by filtering out intensities outside a statistical range using a probability density function.

10. A method comprising:
processing a sample containing a biomarker;
generating mass measurement data of the sample using a Matrix-Assisted Laser Desorption/Ionization Time-of-Flight Mass Spectrometry measurement system;
calibrating the mass measurement data, wherein the calibrating comprises calculating a representative mass of the sample among neighboring masses using center of mass information, and
wherein the center of mass information comprises an intensity weighted sum of masses around a specific mass-to-charge ratio of interest.

11. The method of claim 10, wherein the calibrating comprises:
calculating the center of mass information from the mass measurement data based on interference among neighboring ions of the sample; and calibrating the mass measurement data using the center of mass as the representative mass of the sample.

12. The method of claim 10, wherein the calibrating comprises at least one of:
creating a standard mass-to-charge ratio library;
calibrating the mass measurement data using the standard mass-to-charge ratio library; and
calibrating intensities by filtering out intensities outside a statistical range using a probability density function.

13. The method of claim 10, wherein the calibrating comprises:
calibrating intensities to reduce spot-to-spot variation by finding an average Relative Standard Deviation (RSD) for each scale factor and method, and
selecting the scale factor and method that minimizes the average RDS.

14. The method of claim 10, wherein the method performs at least one of:
disease diagnostics;
microorganism identification;
calibrating mass/charge; or
calibrating intensity data by standard mass analysis through weighted intensity and bracket comparison with normalization through minimum relative standard deviation thresholds by identifying differences in signals of mass and intensity to diagnose at least one of at least one disease or identification of at least one microorganism or biomaterial.

15. The method of claim 14, wherein at least one of:
the biomarker comprises bacteria;
the biomarker comprises a virus;
the biomarker comprises body fluid;
the body fluid comprises at least one of blood or cells;
the biomarker comprises cancer cells;
the at least one disease is a cancer; or
the sample comprises a glycan.

16. The system of claim 1, wherein:
the system comprises an automatic sample processing unit configured to prepare the sample using automation under direction of the control system comprising a plurality processing modules and each of the plurality of processing modules is configured to perform a sample preparation processing task;
the MALDI-TOF MS unit is configured to conduct the at least one measurement on the sample using a laser-shot and generate a distribution of measured data for the laser-shot on the sample under direction of the control system; and
the system comprises at least one handler for moving the sample between at least one of the plurality of processing modules and the MALDI-TOF MS unit.

17. The system of claim 16, wherein the control system is configured to monitor input and output signals of at least one of the plurality of processing modules or the MALDI-TOF MS unit to detect malfunctions.

18. The method of claim 7, wherein at least one of:
the method is for identifying the biomaterial using analysis from the Matrix-Assisted Laser Desorption/Ionization Time-of-Flight Mass Spectrometry;
the method is for minimizing variation in mass and intensity measurement to maximize reproducibility; or
the method comprises providing the calibrated mass measurement data to a biomaterial identification system, wherein the calibrated mass measurement data is compared with known measurement data to identify the biomaterial.

19. The method of claim 10, wherein at least one of:
the method is for diagnosing a disease using the Matrix-Assisted Laser Desorption/Ionization Time-of-Flight Mass Spectrometry system;
the processing the sample comprises processing a patient's sample containing the biomarker to prepare for soft ionization using a matrix;
the method minimizes deviation in mass and intensity variation to maximize reproducibility; or
the method comprises providing the calibrated mass measurement data to a diagnosis system where the calibrated mass measurement data of the biomarker is compared with known measurement data of diseases to identify the disease associated with the biomarker.

20. The system of claim 1, wherein the MALDI-TOF MS is integrated into at least one of a floor-supported hardware unit, a benchtop hardware unit, desktop hardware unit, or a countertop hardware unit.

* * * * *